United States Patent [19]
Jeffers

[11] Patent Number: 5,413,763
[45] Date of Patent: May 9, 1995

[54] METHOD AND APPARATUS FOR REAGENTLESS MEASUREMENT OF THE TOTAL ORGANIC CARBON CONTENT OF AN AQUEOUS SAMPLE

[76] Inventor: Jeff Jeffers, 209 Garfield, LaPorte, Tex. 77571

[21] Appl. No.: 90,492

[22] Filed: Jul. 12, 1993

[51] Int. Cl.$^6$ .................................. G01N 33/00
[52] U.S. Cl. .................................. 422/80; 436/146; 210/758; 96/6; 95/45
[58] Field of Search ............... 436/146; 422/68.1, 80, 422/82.04, 82.05, 186.3; 210/758; 96/6; 95/45; 250/338.1

[56] References Cited

U.S. PATENT DOCUMENTS

| | | | |
|---|---|---|---|
| 4,666,860 | 5/1987 | Blades et al. | 436/146 |
| 4,775,634 | 10/1988 | Sienkiewcz | 436/146 |
| 5,132,094 | 7/1992 | Godec et al. | 422/68.1 |
| 5,244,478 | 9/1993 | Jolly | 55/158 |
| 5,271,900 | 12/1993 | Morita | 422/80 |

OTHER PUBLICATIONS

Godec, Kosenka, Hutte; New Total Organic Carbon Analyzer; SAE Technical Paper Series, #901354; Jul. 9–12, 1990.

Jeffers, Novotny; Process Control Water Quality Monitor for Space Station Freedom–Development Update; SAE Technical Paper Series, #921264; Jul. 13–16, 1992.

Ultrapure Water Expo 1992, pp 53–59; May 11–13, 1992.

Jolly, Jeffers; Ultrapure Water Total Organic Carbon Analyzer–Advanced Component Development; SAE Technical Paper Series, #911436; Jul. 15–18, 1991.

Jeffers, Jolly; Development of the Process Control Water Quality Monitor for Space Station Freedom; SAE Technical Paper Series, #911432; Jul. 15–18, 1991.

*Primary Examiner*—James C. Housel
*Assistant Examiner*—N. Bhat

[57] ABSTRACT

A method and apparatus for the measurement of the total organic carbon (TOC) content of a liquid is shown. The inorganic carbon in the liquid is converted into carbon dioxide and removed from it. At the same time, oxygen is added to the liquid. The liquid is then exposed to ultraviolet radiation and the organic carbon thereby oxidized. This oxidized carbon, in the form of carbon dioxide, is allowed to migrate across a gas-permeable, liquid-impermeable membrane directly into a measurement chamber, where its absorption of radiation is measured to determine its concentration.

11 Claims, 5 Drawing Sheets

METHOD AND APPARATUS FOR REAGENTLESS MEASUREMENT OF THE TOTAL ORGANIC CARBON CONTENT OF AN AQUEOUS SAMPLE

FIELD OF THE INVENTION

This invention relates to a method and apparatus for the measurement of gases dissolved in a liquid. More specifically, it was designed to measure the concentration of carbon dioxide in a sample of purified water for the purpose of determining the total organic carbon (TOC) content of the sample.

BACKGROUND OF THE INVENTION

The measurement of TOC has become a standard method for assessing the level of organic contaminants in purified water. This assessment is necessitated by the demand for purified water in industry and in such closed environments as spacecraft, which have water recycling systems. These systems include components such as the TOC analyzer of the present invention to monitor the quality of the water.

The TOC concentration of a sample of water is generally determined by quantitative analysis of the carbon dioxide generated when organic compounds are oxidized. Several approaches have been disclosed in the prior art. Examples of these approaches are contained in the U.S. Pat. Nos. of Carlson (4,209,299), Ezjak (4,277,438), Blades et al. (4,666,860) and Godec et al. (5,132,094).

Carlson teaches a method of measuring the concentration of a volatile electrolyte, such as carbon dioxide, in a liquid. Carlson's method is to pass a sample stream and a stream of known conductivity on opposite sides of a gas-permeable, liquid-impermeable membrane. The volatile electrolyte in the sample passes through the membrane and into the second liquid. The amount of the volatile electrolyte in the second liquid is then determined by the change in the liquid's conductivity.

Ezjak discloses a similar use of a gas-permeable membrane, but also significantly expands upon its use. Ezjak teaches the introduction of per sulfate ions and oxygen into the sample, followed by irradiation of the sample with ultraviolet (UV) light. This causes the oxidation of organics in the sample and results in carbon dioxide production proportional to the organic content of the sample. The use of UV irradiation in this manner was disclosed by Regan in U.S. Pat. No. 3,958,941. The carbon dioxide gas is then transferred from the sample to a water stream as taught by Carlson.

Ezjak departs from the method of Carlson by then removing the gasses (carbon dioxide) from the water stream in a gas-liquid separator and transporting the gas to an infrared detector. The detector measures absorption of infrared light due to carbon dioxide and the concentration of carbon dioxide is then calculated from the amount of absorption.

Blades et al. discloses a method for measuring TOC which is intended to eliminate the calibration required of a system such as that described by Regan. Blades et al. utilizes a single chamber, transparent on a side, in which a sample is placed and its conductance measured. The sample is then irradiated by UV light while its conductance is continuously monitored. The TOC of the sample is determined from the change in conductance as the sample is irradiated.

Finally, Godec et al. discloses the most common current method for measuring TOC. In the method of Godec, a sample stream is first acidified to facilitate removal of inorganic carbon as carbon dioxide. This carbon dioxide can be transferred from the sample to a water stream and measured by conductive means as in Carlson. Oxidation catalysts are then added to the sample, which is then irradiated by UV light. The carbon dioxide produced by oxidation of the organic carbon is transferred to a water stream and measured conductively.

The most common method of measuring TOC uses elements of all these prior art patents. This method is used in most commercially available (UV)-persulfate analyzers and can be broken down into the following six steps:

1) Acid is injected to lower sample pH to below 4. This converts inorganic carbon from dissolved ionic forms to carbon dioxide gas. Inorganic carbon removal prevents interference with organic carbon detection.
2) This carbon dioxide gas is picked up in a carrier gas stream and separated from the liquid sample in a gravity-dependent Gas-Liquid Separator (GLS).
3) Oxygen is injected to oxidize the carbon present (in the form of water borne organic pollutants) to carbon dioxide gas. The oxygen is in the form of sodium persulfate.
4) Carbon oxidation is enhanced using UV radiation.
5) Carbon dioxide produced by oxidation is picked up in a carrier gas stream and separated from the liquid in a second gravity dependent GLS.
6) The carbon dioxide, via the carrier gas, flows to an infrared (IR) detector where the TOC concentration is determined.

SUMMARY OF THE INVENTION

It is an object of the invention to provide a reagentless method and apparatus for the oxidation of organic carbon in a sample.

It is another object of the invention to provide a simplified method and apparatus for the removal of inorganic carbon and the enhancement of oxidation of a sample.

It is yet another object of the invention to provide a method and apparatus for the conversion of molecular oxygen in the sample to atomic oxygen so that it can oxidize the organic carbon in the sample.

It is yet another object of the invention to provide a TOC analyzer of improved sensitivity.

It is yet another object of the invention to provide a simplified TOC analyzer which does not require the individual steps of separating the organic carbon from the sample and transporting it to a measurement device.

The approach used to measure TOC in the present invention differs from this standard methodology in four significant ways:

1) Sample pH is controlled using a solid-phase acidifier instead of liquid acid injection. The solid phase acidifier allows control of acid addition and uses only the amount of acid that is necessary. The acidifier is consumed with usage and is sized for replacement at regular resupply intervals.
2) Total Organic Carbon (TIC) separation uses a hydrophobic membrane. Membrane separation eliminates dependence on gravity, as well as liquid sparging, thereby avoiding significant loss of volatile organics. Carbon dioxide crosses the membrane and is purged from the GLS with dry, carbon dioxide-free oxygen. Simultaneously, oxygen diffuses across the membrane and provides the sample with essential oxygen for oxidation.

3) UV oxidation, promoted by reactions between dissolved oxygen in the sample and incident radiation, eliminates the complexities of handling and dispensing liquid consumables.

4) Membrane separation of organic carbon dioxide directly into the static Infrared (IR) cell provides maximum sensitivity, eliminates the need for carrier gas, and operates independent of gravity.

In the present invention, a sample stream first flows into a solid phase acidifier (SPA). In the .SPA, the pH of the stream is reduced to below 4 in order to convert the inorganic carbon to $CO_2$.

The stream then flows into a GLS where the inorganic carbon, in the form of $CO_2$, is removed from the stream. This is accomplished by passing the sample stream through a single channel, one side of which is a gas-permeable, liquid-impermeable membrane. In a mirror-image channel on the opposite side of the membrane, oxygen flows in the direction opposite that of the sample stream. As the sample flows through the channel, the $CO_2$ in the sample migrates through the membrane and is carried away by the oxygen stream. At the same time, oxygen migrates through the membrane and into the sample stream. The oxygen which is added to the sample in this manner will later facilitate the oxidation of the organic carbon in the sample in the UV reactor. The use of oxygen instead of oxidizing reagents simplifies and increases the safety of the invention over prior art devices.

The sample stream flows from the GLS to the UV reactor. In the UV reactor, UV radiation emitted by the lamp serves both to convert molecular oxygen in the sample to atomic oxygen and to oxidize the organic carbon in the sample with the atomic oxygen. The oxidation of the organic carbon creates $CO_2$ in the sample which will be measured in the IR cell.

After the organic carbon in the sample is oxidized in the UV reactor, the sample flows to the IR cell. In the IR cell, the sample is again passed through a channel, one side of which is a gas-permeable, liquid-impermeable membrane. On the other side of the membrane is the gas-detection chamber of the IR cell. As the sample flows through the channel, the $CO_2$ migrates through the membrane and directly into the detection chamber. The migration of the $CO_2$ directly into the detection chamber increases the sensitivity of the invention over prior art devices by eliminating the use of a carrier gas to transport the carrier gas from the GLS to the detection chamber.

At one end of the chamber is an IR source. At the opposite end is an IR detector. The absorption of IR energy by the gas in the chamber is measured at several wavelengths, some of which are highly absorbed by the $CO_2$ and some of which are unaffected by the presence of $CO_2$. The $CO_2$ concentration is then determined by comparing the absorption of the $CO_2$-affected wavelengths with that of the $CO_2$-unaffected wavelengths. This comparison of absorbed wavelengths with unabsorbed wavelengths eliminates the need for calibration of the IR cell to determine the intensity of the light in the absence of $CO_2$. These measurements can be made periodically, continuously or after the $CO_2$ concentration has reached equilibrium.

DETAILED DESCRIPTION OF THE PREFERRED EMBODIMENT

Figure 1:
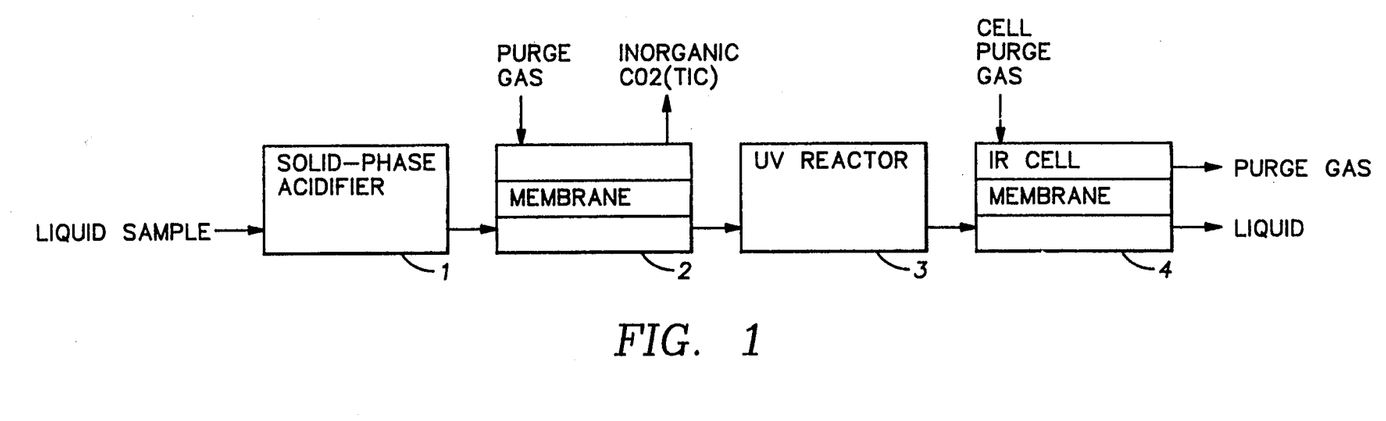
FIG. 1 is a simplified flow schematic of the invention.

Referring to FIG. 1, a schematic diagram of the present invention is shown. A liquid sample flows through a solid phase acidifier 1 and into the pre-reactor GLS 2. Purge gas is pumped into the GLS, carrying away the $CO_2$ which migrates out of the sample and, at the same time, supplying oxygen which migrates across the GLS membrane and into the sample. The sample then flows into the UV reactor 3 where it is irradiated. This causes the molecular oxygen to break down into atomic oxygen and causes the organic carbon in the sample to be oxidized by the atomic oxygen. The sample then flows into the IR cell 4 where the $CO_2$ formed by the oxidation of the organic carbon migrates through a membrane and into the measurement chamber. The concentration of this $CO_2$ is then measured by its absorption of IR radiation.

Figure 2:
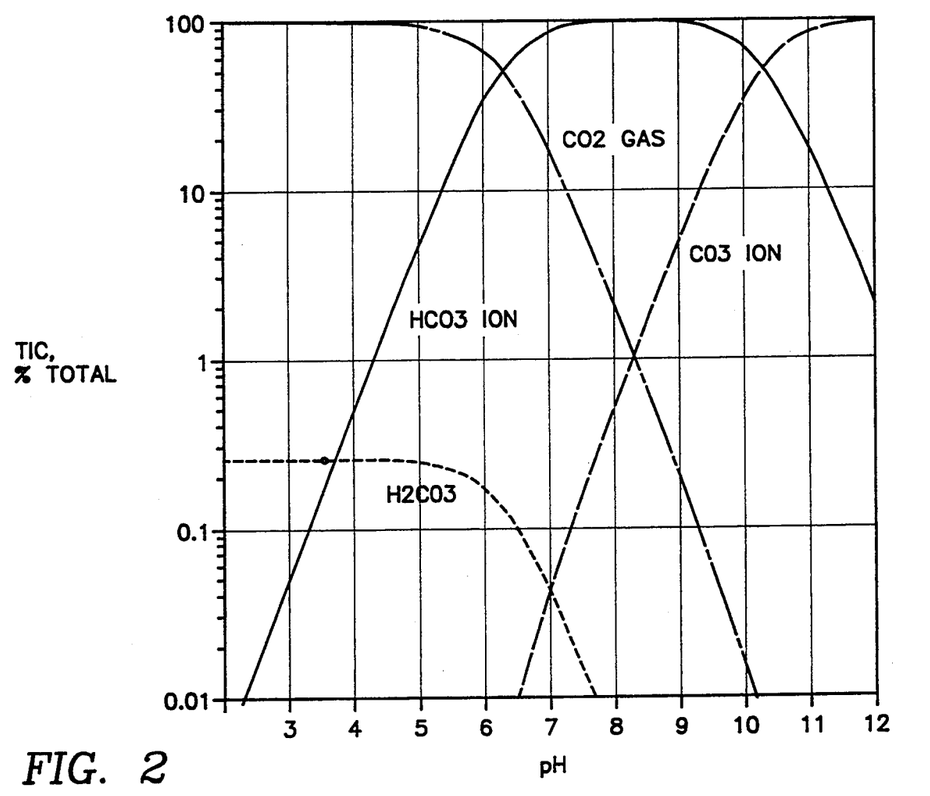
FIG. 2 is a graph of the equilibrium among inorganic constituents of TIC versus pH.

Carbon exists in water in various forms, including dissolved carbon dioxide gas, carbonic acid ($H_2CO_3$), bicarbonate ion ($HCO_3^-$), carbonate ion ($CO_3^{--}$), and organic compounds. The respective concentrations of the different forms of inorganic carbon vary with the pH of the solution in which they are dissolved. FIG. 2 illustrates the equilibrium among inorganic constituents of TIC and quantitative changes in this equilibrium with pH. At a pH below 4, virtually all the inorganic forms are converted to carbon dioxide gas, which may be separated from the liquid sample in a GLS.

Sample pH may be controlled by several techniques, including direct injection of acid into the sample, ion exchange across a membrane, use of an ion exchange bed and dissolution of a slightly soluble solid compound in the sample stream. The preferred embodiment of the present invention uses an SPA to slowly release a solid compound into the water sample, thereby acidifying it. This approach is preferred since it eliminates the need to handle a hazardous liquid, it does not effect sample organics, it is consumed only as needed, and it provides significant weight savings. The invention's SPA as presently designed is a long-life, solid-state, replaceable cartridge measuring a quarter inch in diameter and five inches long.

Since both inorganic and organic carbon are detected and measured as carbon dioxide, the presence of inorganic carbon interferes with the measurement of TOC. Measurement of TOC must therefore account for inorganic carbon. Accounting for inorganic carbon may be done by either: 1) its elimination prior to oxidation to establish a zero baseline for subsequent TOC determination, or 2) separate analyses for inorganic carbon (without oxidation) and total carbon (with oxidation), the difference being equal to TOC.

Eliminating inorganic carbon prior to oxidation is the preferred method, especially when inorganic carbon concentration is sufficiently high to make the cumulative errors introduced by the two separate analyses exceed the desired sensitivity to organic carbon. On the other hand, in applications where dissolved gases are removed during the water reclamation process, total carbon detection may suffice to detect process upset. In this case, an over-limit signal indicates that the dissolved gas and/or the organic removal equipment has malfunctioned. Separate measurements of TIC and TOC may determine which of a number of specific process functions malfunctioned. If TIC measurement is necessary, it can be determined using the invention by .circumventing the UV reactor and the oxygenating GLS which precedes it, and routing the acidified sample directly to the IR GLS and detection cell.

Since sparging is gravity-dependent and causes some loss of volatile organics, it can't be used to remove inorganic carbon in a weightless environment. Another method, membrane Gas-Liquid Separation (GLS), has therefore been ,developed to allow inorganic carbon removal while avoiding these problems. In a test of the GLS technique, less than 10% of acetone was lost, whereas losses in excess of 35% can occur when using sparging.

Inorganic carbon elimination requires that the equilibrium shown in FIG. 2 be shifted to the left (i.e., the pH reduced) for conversion and removal as a gas. Theoretically, as the $CO_2$ is removed, the system moves toward equilibrium and the other forms of inorganic carbon are converted to $CO_2$ until all carbon dioxide and carbon dioxide ionic forms are depleted. In practice, the equilibrium between ionic species can be slow to develop, so the pH is lowered to accelerate gas formation and removal. The preferred embodiment of the invention operates at a pH of less than 4 with sufficient residence time in the pre-reactor GLS to remove virtually all inorganic carbon in the sample up to 20 mg/l. Trace quantities of residual inorganic carbon that remain in the sample are accounted for by periodically measuring the zero-TOC baseline.

Figure 3A:
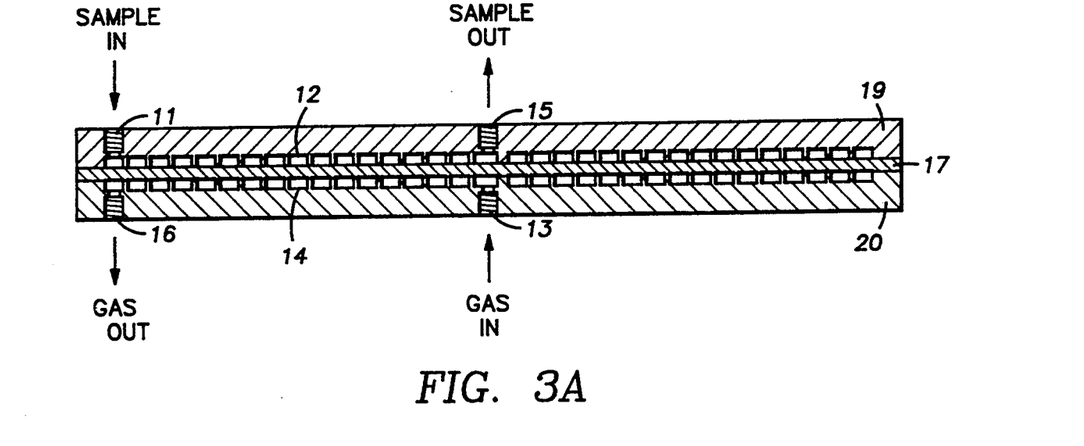
FIGS. 3a and 3b are drawings of the pre-reactor GLS.
Figure 3B:
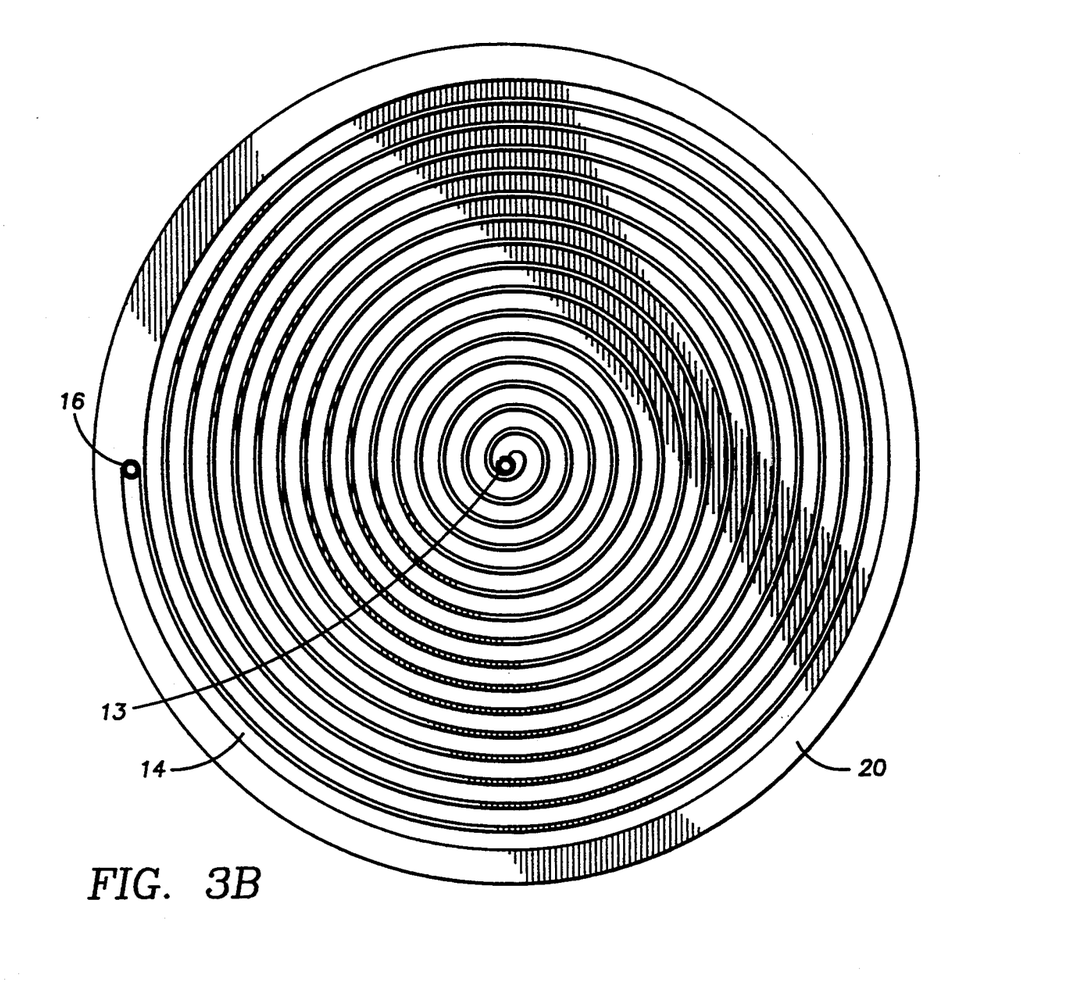
Figure 4A:
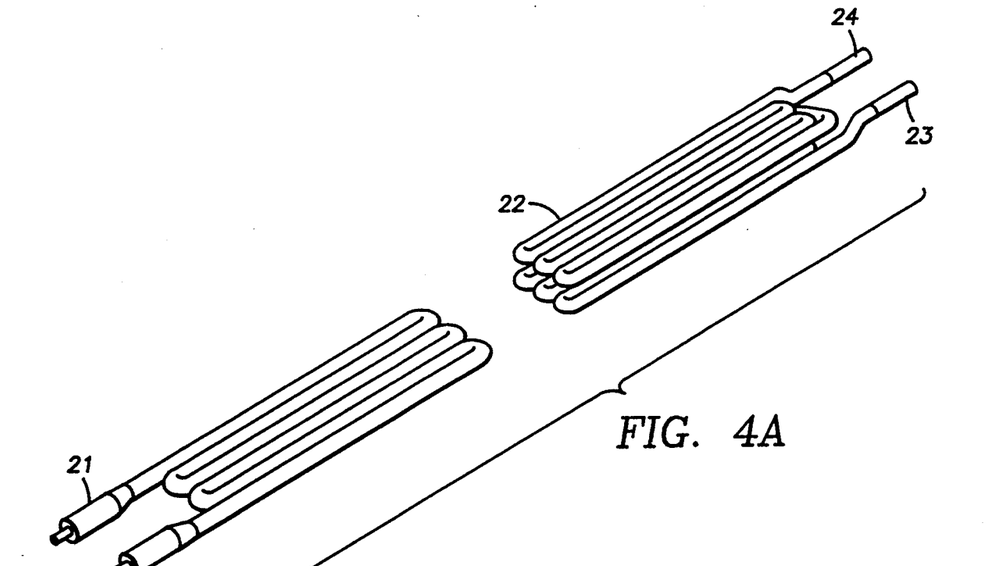
FIG. 4A–D are drawings of the UV reactor.
Figure 4B:
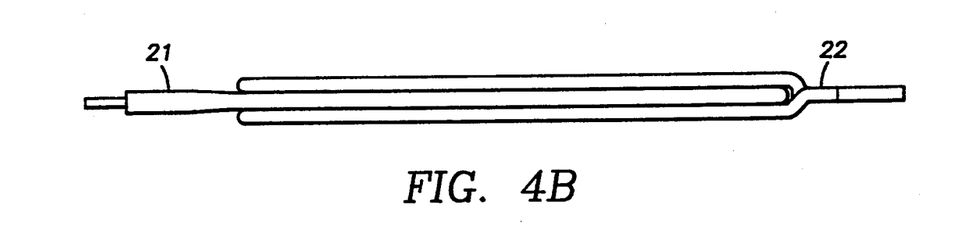
Figure 4C:
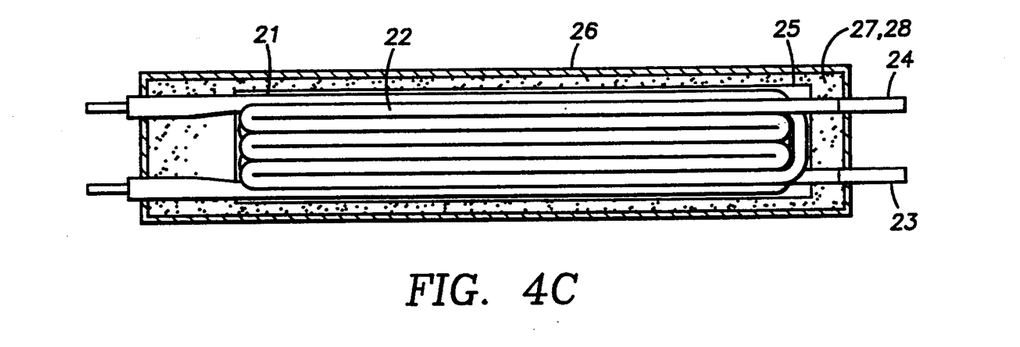
Figure 4D:
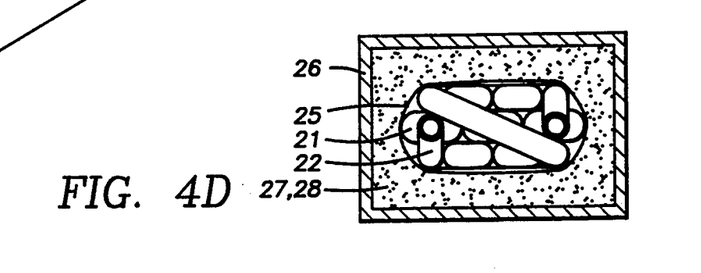

FIG. 3A is a cross-section of the pre-reactor GLS perpendicular to the membrane and intersecting the sample and gas inlets and outlets. FIG. 3B is a diagram of the plate which forms the purge gas channel. Referring to FIGS. 3A and 3B, the acidified sample flows into the pre-reactor GLS through sample inlet 11 and into channel 12. At the same time, oxygen-rich purge gas is made to flow through purge gas inlet 13 and into purge gas channel 14. The sample and the purge gas flow through 12 and 14, respectively, counter-current so that the purge gas enters the GLS next to the sample outlet 15, and exits the GLS next to the sample inlet 11. As the sample and purge gas flow through the channels, the $CO_2$ passes from the sample through the membrane 17 into the purge gas channel. Similarly, oxygen from the purge gas passes through the membrane 17 into the sample channel. After flowing through the entire length of the sample channel, the sample exits through sample outlet 15 and flows to the UV reactor. The purge gas exits through purge gas outlet 16.

The sample channel of the preferred embodiment consists of a spiral passage with the flat membrane forming one wall of the channel. The membrane is sandwiched between two identical facing channels, one side for the sample and the other for gas. The hydrophobic membrane retains the water sample while allowing gas to diffuse across and mix with the purge gas. The difference in partial pressures of $CO_2$ gas in the sample and the purge gas in their respective channels induces carbon dioxide diffusion across the membrane. The difference in partial pressures is maintained by the counter-current flow of the sample and purge gas. Simultaneously, the oxygen in the purge gas diffuses into the sample. This oxygen subsequently supports oxidation of the sample's organics in the reactor.

The pre-reactor GLS of the invention uses a flat membrane with a single flow channel. This selection was made after evaluating both flat membrane and hollow fiber units, which generally showed comparable performance. However, anomalous behavior periodically occurred with hollow fibers. This was attributed to nonuniform carbon dioxide diffusion among the multiple fibers in their parallel-flow configuration. Either or both of two causes are suspected: 1) hollow fiber blockage by trapped gas on the water-side in the fiber end-manifolds, or 2) condensate accumulation on the gas side of the fibers slowing carbon dioxide diffusion to the purge gas stream. The flat membrane is superior because its uniflow path inherently avoids these problems, although the invention can still be practiced with the hollow fibers.

Several microporous hydrophobic membrane materials were evaluated. No difference was detected in the gas recovery performance among these membranes. It was found, however, that flat sheet membranes with laminated support structure had much superior structural integrity and could withstand tearing forces when sealed in the GLS housing.

Several membrane housing materials were evaluated, including FEP-coated aluminum, electropolished stainless steel, and Kynar. Each of these housing materials provided similar performance with no evidence of carbon dioxide sorption. The use of stainless steel provided somewhat better performance in conditions without weight restrictions. Residual inorganic carbon concentrations of less than 30 $\mu gC/l$ with influent as high as 20 mgC/l were obtained with the FEP-coated housing, so FEP-coated aluminum was found to be superior for situations where weight restrictions prevented the use of stainless steel.

The sample leaving the pre-reactor GLS is free of inorganic carbon and has been enriched with molecular oxygen. Referring to FIGS. 4A-4D, the oxygen-enriched sample flows through the sample tube inlet 23 and into the sample tube 22 of the UV reactor. The UV lamp 21 is folded to produce a relatively flat radiative surface or grid. The purpose of the folds is not to produce a rectangular shape, but to allow increased tube length. This is desirable because the energy of the lamp is proportional to this length.

The sample tube 22 lies adjacent to and along the length of the UV lamp 21 and is folded in the same manner. The folds of the sample tube form two flattened volumes, each of which is roughly the same shape as the lamp and adjacent to a side thereof. Through the use of this "sandwiched" configuration, each incremental volume of the sample flows along substantially the same path, traversing the entire length of the UV lamp twice. As the oxygen-enriched sample travels along this path, it is irradiated by the lamp, which serves both to break down the molecular oxygen ($O_2$) into atomic oxygen (O) and to promote the oxidation of the organic carbon with the atomic oxygen. Virtually all of the oxidized carbon is in the form of $CO_2$ because the pH of the sample is less than 4. The sample then exits the tube through outlet 24.

In the preferred embodiment, aluminum foil 25 is wrapped around the lamp and sample tube to reflect back onto the tube the radiation which was not initially absorbed. This foil-wrapped assembly is then placed in housing 26 and the remaining gaps are filled with glass beads 27 and epoxy 28 which conduct heat away from the lamp and also allow thermal expansion.

The UV reactor is designed for maximum utilization of energy from the mercury vapor lamp. The 90 cm lamp provides 100 mw/cm$^2$ at 253.7 nm and 10 mw/cm$^2$ at 184.9 nm. The combination of these wavelengths produces atomic oxygen for effective reagent-less oxidation.

Figure 5:
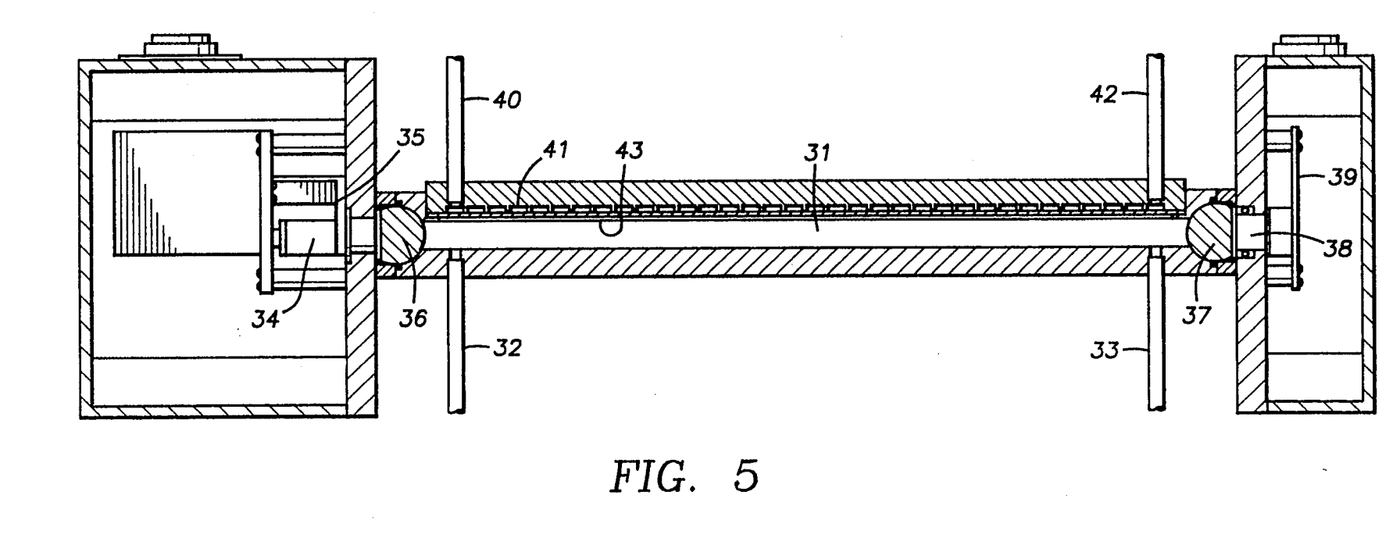
FIG. 5 is a drawings of the IR cell.

Referring to FIG. 5, the detection chamber 31 is purged by gas entering through gas inlet 32 and exiting through gas outlet 33. When the chamber has been purged, inlet 32 and outlet 33 are closed. The sample is then introduced through sample inlet 40 into the sample channel 41 and allowed to exit through sample outlet 42 as the sample flows through channel 41, the $CO_2$ passes through the gas-permeable, liquid-impermeable membrane 43, which forms one wall of the channel, and into the detection chamber 31. Radiation from the IR source 34 passes through the filter blade 35 and lens 36, and into the chamber 31. As the radiation passes through the chamber, some of it is absorbed by the gas in the cell. The remaining radiation passes through lens 37 and falls on detector 38. The signal created by the detector is then processed by the detector electronics 39 and prepared for measurement and/or further processing.

The filter blade of the preferred embodiment serves to keep one of two filters in the optical path between the IR source and detector. The first filter passes 3.8 micrometer radiation which is absorbed by $CO_2$. The second passes 4.3 micrometer radiation which is not absorbed by $CO_2$. Comparison of the absorption at these two wavelengths allows the determination of the $CO_2$ concentration. The absorption of the gas in the cell can be measured continuously, at discrete intervals or after the sample reaches equilibrium.

Carbon dioxide concentration in the cell exponentially approaches equilibrium with the flowing water sample. Equilibrium exists when the two partial pressures are equal. When sample concentration increases, the cell concentration rises at a rate proportional to the change in sample concentration. Likewise, when the sample concentration decreases, the cell concentration decreases at a predictable rate.

EQ (1) shows the sample partial pressure relationship to the partial pressure measured in the IR cell.

$$Pi = P1 + [(P2-P1)/(1-k1)] \quad (1)$$

$$k1 = \exp[-Qw/Ve*(t2-t1)]$$

$$Ve = Vc/(1-k2)$$

$$k2 = \exp(-G*A*1E6/Qw)$$

Where:

| | | |
|---|---|---|
| Pi | = | Partial pressure of water sample, ppm carbon dioxide |
| | = | IR cell partial pressure at equilibrium, ppm carbon dioxide |
| P1 | = | Cell partial pressure at an earlier time, t1 minutes, ppm carbon dioxide |
| P2 | = | Cell partial pressure at time, t2 minutes, ppm carbon dioxide |
| Qw | = | Sample flow rate, cc/min |
| Ve | = | Effective volume of IR cell, cc |
| | = | Vc/Fraction of gas recovered |
| | = | Vc/(1−k2) |
| Vc | = | Geometric volume of IR cell, cc |
| A | = | Mass transfer area of membrane, cm$^2$ |
| G | = | Mass transfer coefficient between sample and cell, cc/min-cm$^2$-ppm |

EQ (1) shows that when the IR cell signal is read periodically, for example once every 10 seconds, a single near real-time value of the equilibrium partial pressure can be computed from the two IR absorption values. As is shown below, these are directly proportional to TOC. Continuously repeating this procedure provides organic carbon values updated every 10 seconds.

The cell equilibrates with the carbon dioxide partial pressure in the water sample. The equilibrium between the free gaseous $CO_2$ in the chamber and the dissolved $CO_2$ in the sample is described by EQ (2), which is known as Henry's Law.

$$H_{CO2} = P_{CO2}/M_{CO2}$$

where

| | | |
|---|---|---|
| $H_{CO2}$ | = | the Henry's Law constant for $CO_2$ |
| | = | $\exp(-5789.04/T - 11.4519?T - 0.010454\ T + 94.4914)$ (atm.kg/mole) |
| T | = | °K |
| $P_{CO2}$ | = | partial pressure of $CO_2$ in the chamber (atm.kg) |
| $M_{CO2}$ | = | molality of $CO_2$ in the sample (mole/kg) |

The concentration of $CO_2$ in the sample can be determined from EQ (2) as rewritten in EQ (3).

$$C_{CO2} = 12{,}010{,}000(\mu g/mole) \cdot P_{CO2}/H_{CO2}$$

where $$C_{CO2} = \text{sample } CO_2 \text{ concentration } (\mu g/kg)$$

EQ (3) also assumes that the specific gravity of the sample is very close to 1.0000, so that $\mu g/kg = \mu g/L$.

Figure 6:
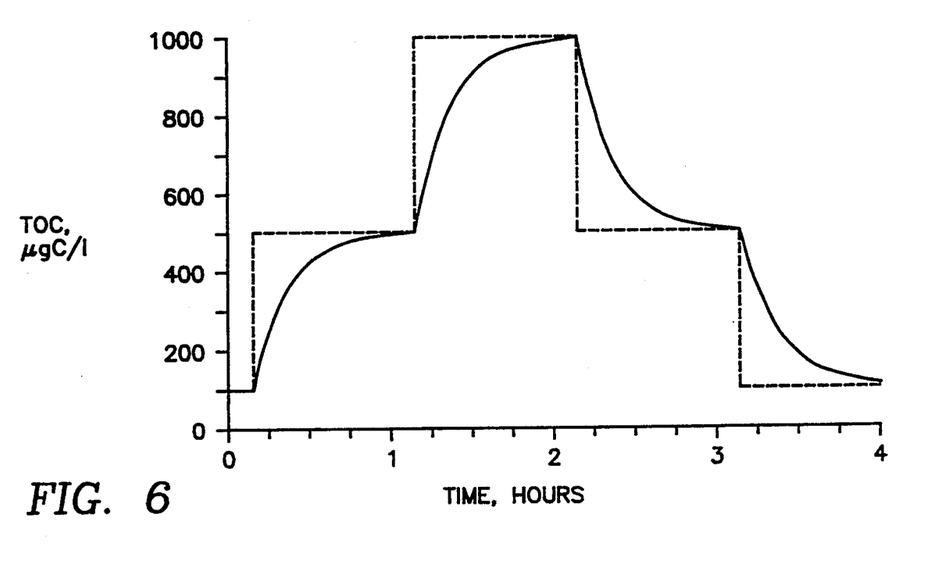
FIG. 6 is a graph of IR signal response time to sample TOC.

FIG. 6 shows how the IR signal response varies with respect to sample TOC. The IR signal responds to a sequence of step changes from 100 to 500 to 1,000 to 500 to 100 $\mu gC/l$ reflecting a cell concentration which exponentially approaches each new equilibrium. The change in sample concentration is detected and the new TOC value is reported immediately based on the rate of change in cell concentration, which is directly related to the difference in current cell concentration and the new sample equilibrium value.

Figure 7:
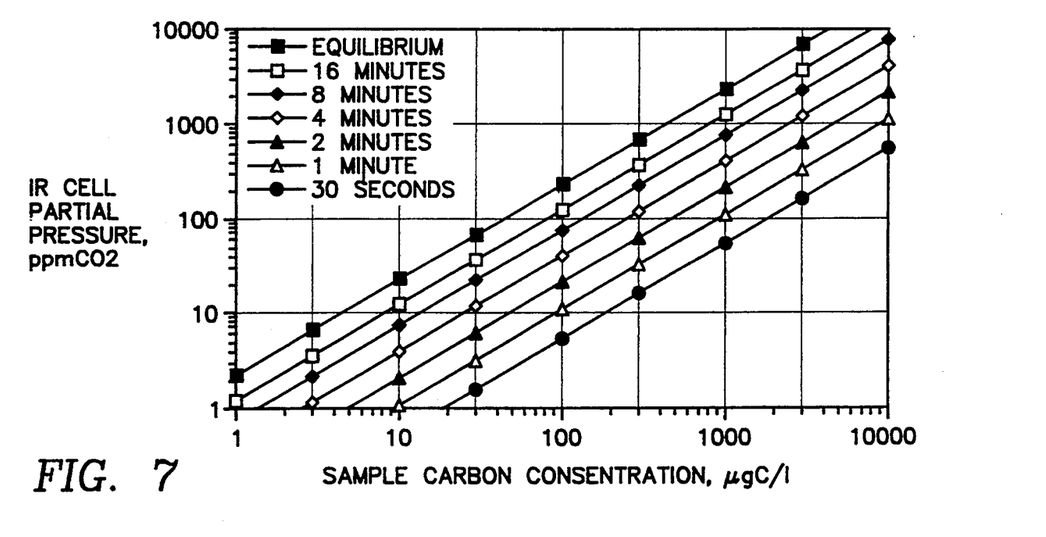
FIG. 7 is a graph of IR cell concentration versus sample TOC at discrete times after cell purge with carbon dioxide-free gas.

FIG. 7 shows the linear relationship between sample TOC and cell concentration at discrete times after cell purge with carbon dioxide-free gas. The IR detection cell can detect a minimum of 3 ppm carbon dioxide. This corresponds to a minimum TOC detection level of less than 2 $\mu gC/l$ at equilibrium.

In the IR detection cell, IR radiation emitted from an incandescent source passes through the gas cell containing the recovered carbon dioxide gas and is then received at a solid-state detector. Carbon dioxide absorbs radiation at a wavelength of 3.8 micrometers, thereby reducing the detected light intensity with increasing concentration. The IR bench uses a moveable filter flag to select one of two wavelengths of light to be applied to the gas cell. The analytical filter passes infrared radiation centered at 3.8 micrometers which is absorbed by carbon dioxide, while the reference filter, centered at 4.3 micrometers, passes wavelengths which are not absorbed by carbon dioxide. The intensity at this reference wavelength provides a stable baseline to compensate for changes in light source, detector, or cell optical characteristics due to aging or surface fouling.

Figure 8:
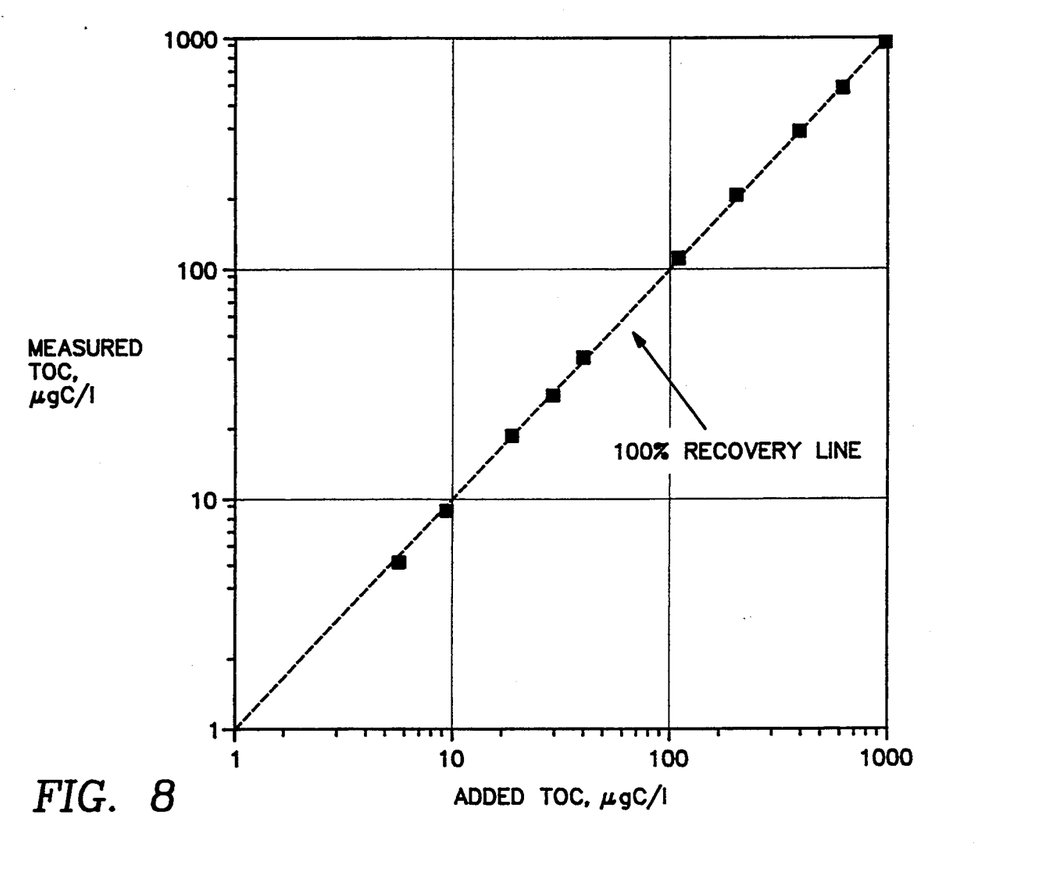
FIG. 8 is a graph of measured TOC versus added TOC for tests on ethylene glycol.

FIG. 8 shows the results of TOC-added tests. Known volumes (0.5 to 30 cc) of 10 mgC/l stock TOC solution were incrementally added to a beginning volume of 2 liters of UV-polished Milli-Q water (this water typically has <25 $\mu$gC/l background TOC). Following each addition the sample was automatically processed through the prototype of the invention where the carbon dioxide partial pressure produced by carbon oxidation reached equilibrium with the IR cell. TOC was then computed based on this equilibrium partial pressure. The standard error for this test was <10 $\mu$gC/l in the range from 5 to 1,000 $\mu$gC/l.

Samples were tested using the prototype of the invention to determine both TOC levels and TOC recovery. TOC recovery was tested by presaturating the sample with oxygen to ensure an excess of oxygen and operating two UV reactors in series. In one configuration, a GLS removed the carbon dioxide generated in the first reactor. The residual organic carbon in the sample was then oxidized by the second reactor. Thus, the carbon dioxide subsequently recovered in the IR/GLS represented the organic carbon not oxidized by the first reactor. In the second configuration, the two reactors were operated directly in series. Any increase in TOC when both reactors were turned on thus indicated unoxidized inorganic carbon from a single operating reactor. The test results showed essentially complete oxidation by the invention, with the unrecovered organic carbon <5 $\mu$gC/l.

These configurations were also tested using a sample containing urea, which is notorious for its resistance to oxidation. In this test series, the reactor oxidized all but 25 $\mu$gC/l of the 500 $\mu$gC/l sample for 95% recovery. These tests show that at least 95% recovery of organic contaminants can be expected by the present invention.

I claim:

1. A reagentless UV reactor for the oxidation of organic carbon in an aqueous sample, comprising:
   a gas-liquid separator;
   said gas-liquid separator having a sample channel through which a aqueous sample can flow and a purge gas channel through which a purge gas can flow;
   said sample channel and said purge gas channel being adjacent to each other and sharing a gas-permeable, liquid-impermeable membrane common wall;
   said sample channel and said purge gas channel each having an inlet at a first end and an outlet at a second end;
   said first end of said purge gas channel being adjacent to said second end of said sample channel so that said sample and said purge gas flow countercurrent;
   said purge gas containing molecular oxygen ($O_2$);
   a UV reactor;
   said UV reactor having a sample tube;
   said UV reactor having a UV lamp;
   said UV lamp emitting ionizing radiation at a wavelength which breaks down molecular oxygen ($O_2$) into atomic oxygen (O);
   said UV lamp emitting oxidizing radiation at a wavelength which promotes oxidization of organic carbon in said sample;
   said sample tube being at least partially transparent to said ionizing radiation and said oxidizing radiation;
   said sample tube being positioned so that said ionizing radiation and said oxidizing radiation pass therethrough;
   said sample outlet of said gas-liquid separator being connected to said sample inlet of said UV reactor so that said sample flows through said gas-liquid separator and then through said UV reactor.

2. The reagentless UV reactor of claim 1 wherein said purge gas comprises essentially pure molecular oxygen.

3. The reagentless UV reactor of claim 1 further comprising a reflective sheath wherein said sheath surrounds said UV lamp and said sample tube and reflects said radiation back onto said sample tube.

4. The reagentless UV reactor of claim 1 wherein said UV lamp comprises a 90 centimeter mercury vapor lamp.

5. The reagentless UV reactor of claim 1 wherein said UV amp emits radiation having wavelengths of 253.7 nm and 184.9 nm.

6. The reagentless UV reactor of claim 1 wherein the depth of said sample channel from said membrane is small.

7. The reagentless UV reactor of claim 1 wherein said sample channel and said purge gas channel form spirals.

8. The reagentless UV reactor of claim 1 wherein said UV lamp is folded to form a flat grid.

9. A reagentless UV reactor for the oxidation of organic carbon in an aqueous sample, comprising:
   a gas-liquid separator;
   said gas-liquid separator having a plurality of hollow fibers through which a aqueous sample can flow;
   said hollow fibers being made of a gas-permeable, liquid-impermeable material;
   said hollow fibers having an inlet manifold which distributes said sample to said fibers and an outlet manifold which collects said sample flowing out of said fibers
   said hollow fibers being enveloped by an enclosure having a purge gas inlet and a purge gas outlet;
   said inlet manifold being positioned opposite said purge gas inlet so that purge gas entering said enclosure flows countercurrent to said sample flowing through said fibers;
   said purge gas containing molecular oxygen ($O_2$);
   a UV reactor;
   said UV reactor having a sample tube;
   said UV reactor having a UV lamp;
   said UV lamp emitting ionizing radiation at a wavelength which breaks down molecular oxygen ($O_2$) into atomic oxygen (O);
   said UV lamp emitting oxidizing radiation at a wavelength which promotes oxidization of organic carbon in said sample;

said sample tube being at least partially transparent to said ionizing radiation and said oxidizing radiation;

said sample tube being positioned so that said ionizing radiation and said oxidizing radiation pass therethrough;

said sample outlet of said gas-liquid separator being connected to said sample inlet of said UV reactor so that said sample flows through said gas-liquid separator and then through said UV reactor.

10. The reagentless UV reactor of claim 9 wherein said sample tube is folded to form a grid of essentially the same shape as said UV lamp and said sample tube grid is positioned adjacent to and parallel to said lamp grid.

11. The reagentless UV reactor of claim 9 wherein said sample tube is folded to form a first grid and a second grid of essentially the same shape as said UV lamp grid, each of said sample tube grids being positioned parallel to and adjacent to opposite sides of said lamp grid.

* * * * *